United States Patent [19]

Mihara et al.

[11] Patent Number: 5,024,917

[45] Date of Patent: Jun. 18, 1991

[54] OPTICAL RECORDING MEDIUM CONTAINING META-POSITION ALUMINIUM-TYPE IR-RAY ABSORPTIVE COMPOUND

[75] Inventors: Chieko Mihara, Kawaski; Tsuyoshi Santoh, Yokohama; Hiroyuki Sugata, Yamato, all of Japan

[73] Assignee: Canon Kabushiki Kaisha, Tokyo, Japan

[21] Appl. No.: 440,073

[22] Filed: Nov. 22, 1989

[30] Foreign Application Priority Data

Nov. 28, 1988 [JP] Japan ................................ 63-298373

[51] Int. Cl.$^5$ .......................... G03C 1/00; B32B 3/02; G11B 11/03
[52] U.S. Cl. .................................... 430/271; 430/270; 430/495; 430/945; 428/64; 346/135.1
[58] Field of Search ............... 430/495, 270, 945, 271; 346/135.1; 428/64

[56] References Cited

U.S. PATENT DOCUMENTS

| | | | |
|---|---|---|---|
| 3,251,881 | 5/1966 | Susi et al. | 260/576 |
| 3,484,467 | 12/1969 | Susi et al. | 260/440 |
| 3,575,871 | 4/1971 | Susi et al. | 252/300 |
| 4,656,121 | 4/1987 | Sato et al. | 430/495 |
| 4,871,601 | 10/1989 | Miura et al. | 428/64 |
| 4,892,606 | 1/1990 | Miyazaki et al. | 156/275.5 |

FOREIGN PATENT DOCUMENTS 61-069991 4/1986 Japan .

*Primary Examiner*—Charles L. Bowers, Jr.
*Assistant Examiner*—Ashley I. Pezzner
*Attorney, Agent, or Firm*—Fitzpatrick, Cella, Harper & Scinto

[57] ABSTRACT

The present invention provides an IR-ray absorptive compound having a specific structural formula and an optical recording medium. The IR-ray absorptive compound has excellent characteristics that absorption in the infrared region is large and improved in solvent solubility.

In corporation of the IR-ray absorptive compound into a thin film containing an organic coloring matter of an optical recording medium has remarkably improved the storage stability and the light resistance of the medium. Further the high solubility in solvents prevents formation of a solid in the recording layer, whereby the optical recording medium having a low noise level can be obtained.

6 Claims, No Drawings

OPTICAL RECORDING MEDIUM CONTAINING META-POSITION ALUMINIUM-TYPE IR-RAY ABSORPTIVE COMPOUND

BACKGROUND OF THE INVENTION

1. Field of the Invention

The present invention relates to an IR-ray absorptive compound and an optical recording medium utilizing the same. In particular, the present invention pertains to an IR-ray absorptive compound which provides an optical recording medium with improved durability in repeated reproduction and light resistance.

2. Related Background Art

Generally, optical recording media such as, for example, optical discs or optical cards record information at high density using optically detectable small pits (of approximately 1 μm) on a thin recording layer provided on a substrate having a spiral, circular or linear groove thereon. By scanning a laser beam converged on the surface of the recording layer, the recording layer absorbs laser energy to form the optically detectable pits.

According to a heat mode recording system, the recording layer absorbs heat energy and forms a small concave portion (the pit) through evaporation or melting at that site. By using an organic dye thin film to provide a recording layer with high reflectance, the optical contrast of the recording pit can be set at a high level. For example, when polymethine, azulene, cyanine or pyrylium type dyes, etc. having high light absorption relative to laser beam are used for the organic dye thin film, a light absorptive reflective film exhibiting metallic luster (i.e., a reflectance of 10 to 50%) can be obtained, whereby an optical recording medium capable of laser recording and reflective reading can be obtained. Additionally, when a semiconductor laser with an oscillation wave length of 600 to 800 nm is used as the laser light source, there is the particular advantage that the device can be made smaller in size and with lower cost. However, organic dye thin films had the problems that recording and reproduction characteristics and storage stability may be lowered, because they generally deteriorate upon the application of heat and light, etc.

To cope with such problems, U.S. Pat. No. 4,656,121 has proposed a method to improve light resistance by incorporating an aminium salt or diimonium salt of a triarylamine type compound incorporated in a polymethine type dye.

SUMMARY OF THE INVENTION

An object of the present invention is to provide an IR-ray absorptive compound improved light resistance and repeated reproduction durability, and which exhibits solvent solubility greater than the prior art.

Another object of the present invention is to provide an optical recording medium with improved light resistance and repeated reproduction durability, with good productivity.

More specifically, the IR-ray absorptive compound of the present invention is represented by the following formula (I):

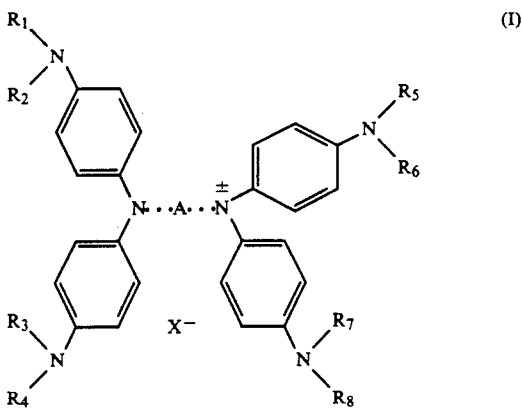

where A is

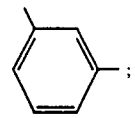

$R_1$ to $R_8$ are hydrogen, halogen, or a univalent organic radical, or at least one of the combinations of the atomic groups of $R_1$ and $R_2$, $R_3$ and $R_4$, $R_5$ and $R_6$, and $R_7$ and $R_8$ forms together with the nitrogen a substituted or unsubstituted five-, six- or seven-membered heterocycle; the $R_1$ to $R_8$ being the same or different; the combinations of $R_1$ and $R_2$, $R_3$ and $R_4$, $R_5$ and $R_6$, and $R_7$ and $R_8$ being the same or different; and $X^-$ is an anion. The optical recording medium of the present invention contains at least one of the IR-ray absorptive compounds represented by the formula (I).

DESCRIPTION OF THE PREFERRED EMBODIMENTS

The inventors believe that in the IR-ray absorptive compound of the formula [I] above, the meta-position substitution of the central benzene ring disturbs the linearity of the whole molecule such that the, solvent solubility of the compounds increases.

In formula (I), $R_1$ to $R_8$ are hydrogen, halogen, or a univalent organic radical. The halogen includes fluorine, chlorine, bromine, and iodine. The univalent organic radical includes a substituted or unsubstituted alkyl, a substituted or unsubstituted alkoxy, a substituted or unsubstituted alkoxyalkyl, a substituted or unsubstituted alkenyl, a substituted or unsubstituted alkynyl, and a substituted or unsubstituted aralkyl.

Specifically, the unsubstituted alkyl radicals includes methyl, ethyl, n-propyl, isopropyl, n-butyl, isobutyl, t-butyl, n-amyl, t-amyl, n-hexyl, n-octyl, t-octyl, etc., and the substituted alkyl radicals includes 2-hydroxyethyl, 3-hydroxypropyl, 4-hydroxybutyl, 2-acetoxyethyl, carboxymethyl, 2-carboxyethyl, 3-carboxypropyl, etc.

The alkoxyalkyl radicals include linear or branched alkoxyalkyls such as methoxymethyl, 2-methoxyethyl, 3-methoxypropyl, 2-methoxypropyl, 4-methoxybutyl, 3-methoxybutyl, 2-methoxybutyl, 5-methoxypentyl, 4-methoxypentyl, 3-methoxypentyl, 2-methoxypentyl, 6-methoxyhexyl, ethoxymethyl, 2-ethoxyethyl, 3-ethoxypropyl, 2-ethoxypropyl, 4-ethyoxybutyl, 3-ethoxybutyl, 5-ethoxypentyl, 4-ethoxypentyl, 6-ethoxyhexyl, propoxymethyl, 2-propoxyethyl, 3-propoxypropyl, 4-propoxybutyl, 5-propoxypentyl, etc.

The alkoxy radicals include methoxy, ethoxy, propoxy, butoxy, etc. The alkenyl radicals include vinyl, propenyl, butenyl, pentenyl, hexenyl, heptenyl, octenyl, etc.

The aralkyl radicals include benzyl, p-chlorobenzyl, p-methylbenzyl, 2-phenylmethyl, 2-phenylpropyl, 3-phenylpropyl, α-naphtylmethyl, β-naphthylethyl, etc. The alkynyl radicals include propargyl, butynyl, pentynyl, hexynyl, etc.

In particular, radicals having 1-8 carbons are preferred, and alkoxyalkyl, alkenyl and alkynyl radicals will give IR-ray absorptive compounds with excellent solvent solubility.

The substituted or unsubstituted five-membered ring formed by at least one of the combinations of $R_1$ and $R_2$, $R_3$ and $R_4$, $R_5$ and $R_6$, and $R_7$ and $R_8$ together with the nitrogen includes a pyrrolidine ring, etc.; the substituted or unsubstituted six-membered ring includes a piperidine ring, a morpholine ring, a tetrahydropyridine ring, etc.; and the substituted or unsubstituted seven-membered ring formed thereby includes hexamethyleneimine ring, etc. The respective combinations may be the same or different. The formation of the ring from $R_n$ and $R_{n+1}$ (n is 1, 3, 5, or 7) gives IR-ray absorptive compounds exhibiting more stabilizing effect.

$X^-$ represents anions including chloride, bromide, iodide, perchlorate, nitrate, benzenesulfonate, p-toluenesulfonate, methylsulfate, ethylsulfate, propylsulfate, tetrafluoroborate, tetraphenylborate, hexafluorophosphate, benzenesulfinate, acetate, trifluoroacetate, propionate, benzoate, oxalate, succinate, malonate, oleate, stearate, citrate, hydrogenphosphate, dihydrogenphosphate, pentachlorostannate, chlorosulfonate, fluorosulfonate, trifluoromethansulfonate, hexafluoroarsenate, hexafluoroantimonate, molybdate, tungstate, titanate, zirconate, etc.

In formula [I], A denotes

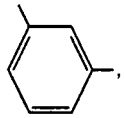

which may be substituted by a lower alkyl radical, a lower alkoxy radical, a halogen radical, or a hydroxyl radical.

The IR-ray absorptive compound of the present invention may be manufactured according to methods described in U.S. Pat. Nos. 3,251,881, 3,575,871, or 3,484,467, and Japanese Patent Laid-open Publication No. 61-69991 (1986). For example, it may be manufactured by the process below:

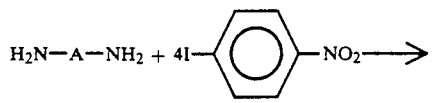

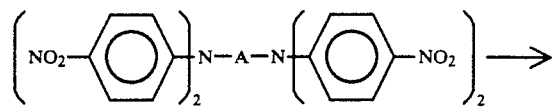

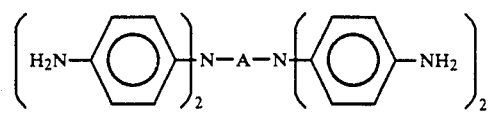

where A denotes

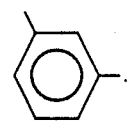

The amine prepared by the above Ullmann reaction and the reducing reaction is alkylated alkenylated, aralkylated or alkynylated, by selective substitution, and then oxidized to give the final product. In a case where $R_1$ to $R_8$ are not symmetrical, the alkylation needs to be conducted in multiple stages. Accordingly, from the standpoint of the manufacturing cost, $R_1$ to $R_8$ are preferably the same.

Various specific examples of the IR-ray absorptive compounds represented by the present invention are shown below. For simplicity, the compounds are shown in a form of X, A, ($R_1R_2$) ($R_3R_4$) ($R_5R_6$) ($R_7R_8$).

For example, in Formula (I), if $X^-$ is $ClO_4^-$, A is

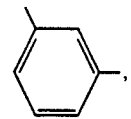

and $R_1$ to $R_8$ are respectively isopropyl, the compound is denoted as:

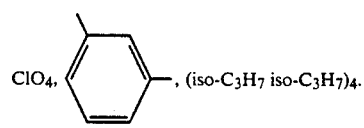

| Compound No. | |
| --- | --- |
| (I)-1 | 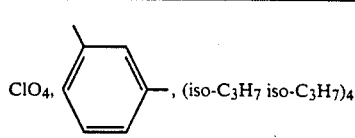 |

-continued
| Compound No. | | |
|---|---|---|
| (I)-2 | 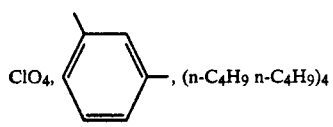 ClO4, , (n-C4H9 n-C4H9)4 | |
| (I)-3 | 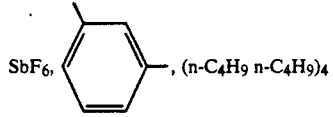 SbF6, , (n-C4H9 n-C4H9)4 | |
| (I)-4 | 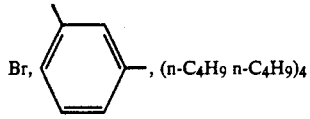 Br, , (n-C4H9 n-C4H9)4 | |
| (I)-5 | 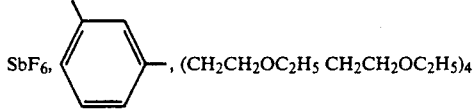 SbF6, , (CH2CH2OC2H5 CH2CH2OC2H5)4 | |
| (I)-6 | 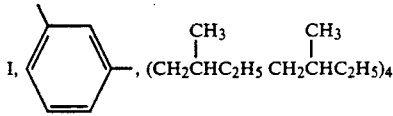 I, , (CH2$\overset{CH_3}{\overset{|}{C}}$HC2H5 CH2$\overset{CH_3}{\overset{|}{C}}$HC2H5)4 | |
| (I)-7 | 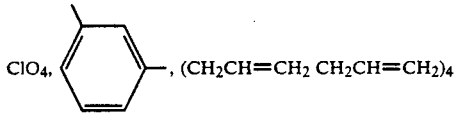 ClO4, , (CH2CH=CH2 CH2CH=CH2)4 | |
| (I)-8 | 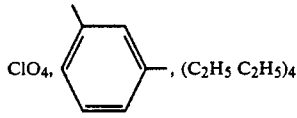 ClO4, , (C2H5 C2H5)4 | |
| (I)-9 | 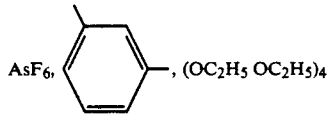 AsF6, , (OC2H5 OC2H5)4 | |
| (I)-10 | 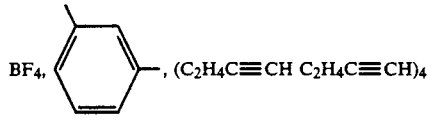 BF4, , (C2H4C≡CH C2H4C≡CH)4 | |
| (I)-11 | 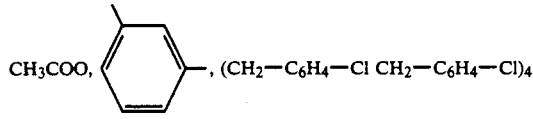 CH3COO, , (CH2—C6H4—Cl CH2—C6H4—Cl)4 | |
| (I)-12 | 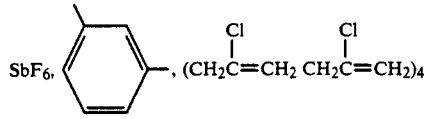 SbF6, , (CH2$\overset{Cl}{\overset{|}{C}}$=CH2 CH2$\overset{Cl}{\overset{|}{C}}$=CH2)4 | |

-continued

| Compound No. | |
|---|---|
| (I)-13 | ClO$_4$, 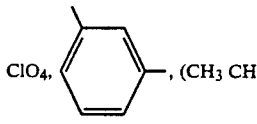, (CH$_3$ CH$_3$)$_4$ |
| (I)-14 | ClO$_4$, 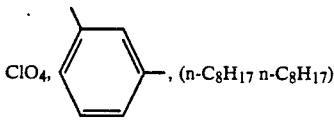, (n-C$_8$H$_{17}$ n-C$_8$H$_{17}$)$_4$ |
| (I)-15 | AsF$_6$, 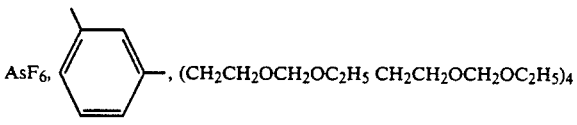, (CH$_2$CH$_2$OCH$_2$OC$_2$H$_5$ CH$_2$CH$_2$OCH$_2$OC$_2$H$_5$)$_4$ |
| (I)-16 | ClO$_4$, 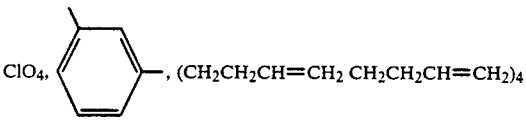, (CH$_2$CH$_2$CH=CH$_2$ CH$_2$CH$_2$CH=CH$_2$)$_4$ |
| (I)-17 | SbF$_6$, 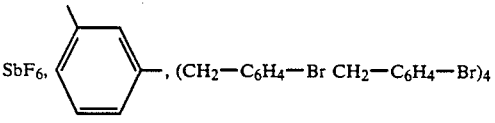, (CH$_2$—C$_6$H$_4$—Br CH$_2$—C$_6$H$_4$—Br)$_4$ |
| (I)-18 | Br, 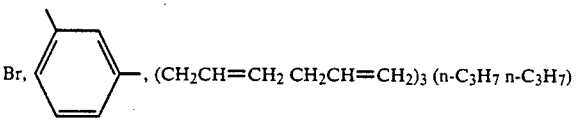, (CH$_2$CH=CH$_2$ CH$_2$CH=CH$_2$)$_3$ (n-C$_3$H$_7$ n-C$_3$H$_7$) |
| (I)-19 | AsF$_6$, 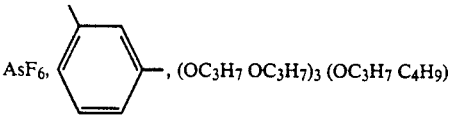, (OC$_3$H$_7$ OC$_3$H$_7$)$_3$ (OC$_3$H$_7$ C$_4$H$_9$) |
| (I)-20 | ClO$_4$, 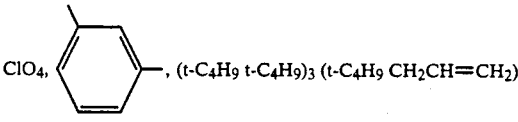, (t-C$_4$H$_9$ t-C$_4$H$_9$)$_3$ (t-C$_4$H$_9$ CH$_2$CH=CH$_2$) |
| (I)-21 | BF$_4$, 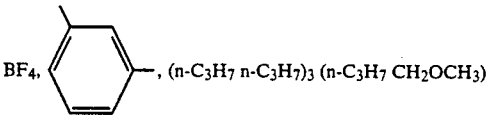, (n-C$_3$H$_7$ n-C$_3$H$_7$)$_3$ (n-C$_3$H$_7$ CH$_2$OCH$_3$) |
| (I)-22 | AsF$_6$, Cl—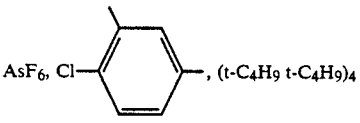, (t-C$_4$H$_9$ t-C$_4$H$_9$)$_4$ |
| (I)-23 | SbF$_6$, Cl—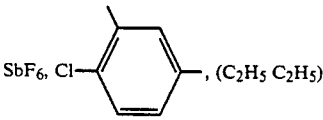, (C$_2$H$_5$ C$_2$H$_5$)$_4$ |

-continued
| Compound No. | |
|---|---|
| (I)-24 | 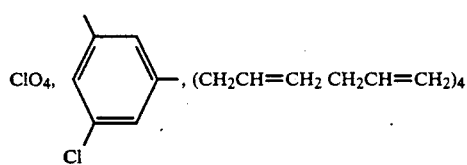 |
| (I)-25 | 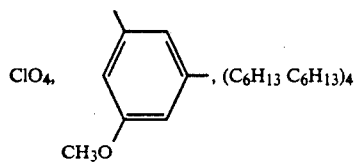 |
| (I)-26 | 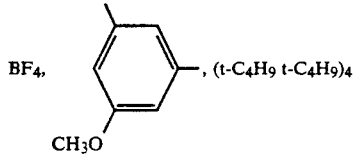 |
| (I)-27 | 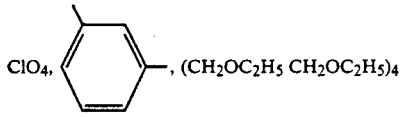 |
| (I)-28 | 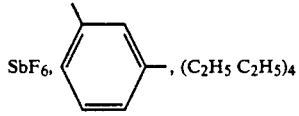 |
| (I)-29 | 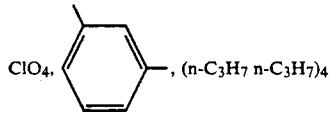 |
| (I)-30 | 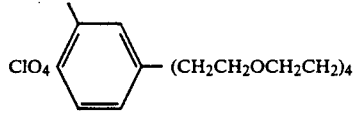 |
| (I)-31 | 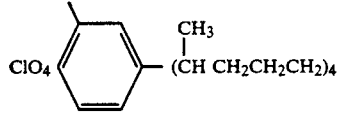 |
| (I)-32 | 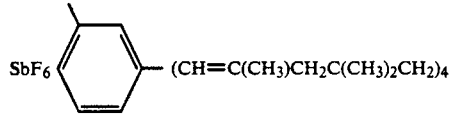 |
| (I)-33 | 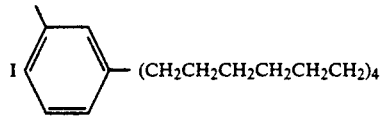 |

-continued
| Compound No. | |
|---|---|
| (I)-34 | 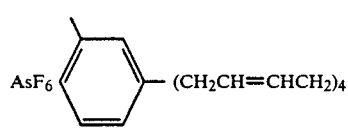 |
| (I)-35 | 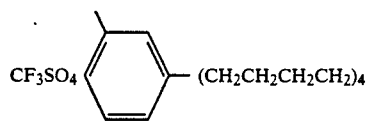 |
| (I)-36 | 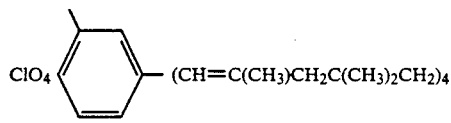 |
| (I)-37 | 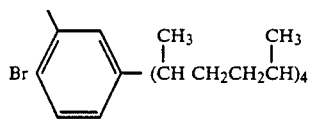 |
| (I)-38 | 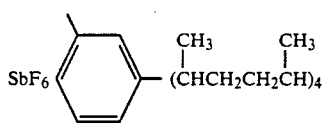 |
| (I)-39 | 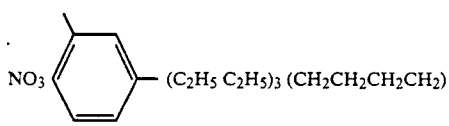 |
| (I)-40 | 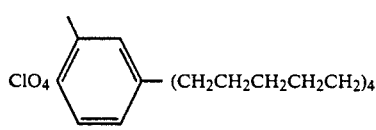 |
| (I)-41 | 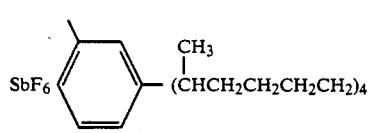 |
| (I)-42 | 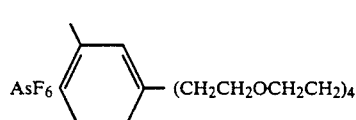 |
| (I)-43 | 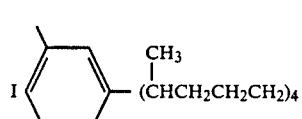 |
| (I)-44 | 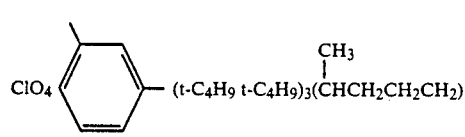 |

-continued

| Compound No. | |
|---|---|

(I)-45

ClO₄ — [benzene ring with CH₃ top, Cl bottom] — (CHCH₂CH₂CH₂)₄ with CH₃ substituent (I)-46

I — [benzene ring with CH₃ top, CH₃ bottom] — (CH=C(CH₃)CH₂C(CH₃)₂CH₂)₄

(I)-47

SbF₆ Cl — [benzene ring with CH₃ top] — (CH₂CH₂CH₂CH₂)₄

(I)-48

ClO₄ — [benzene ring with CH₃ top, OH bottom] — (CH₂CH₂OCH₂CH₂)₄

(I)-49

AsF₆ — [benzene ring with CH₃ top, CH₃O bottom] — (CHCH₂CH₂CH₂CH)₄ with two CH₃ substituents (I)-50

SbF₆ — [benzene ring with CH₃ top, Br bottom] — (CH₂CH₂OCH₂CH₂)₄

(I)-51

NO₃ CH₃O — [benzene ring with CH₃ top, CH₃O bottom] — (C₂H₅ C₂H₅)₃(CH₂CH₂CH₂CH₂)

The IR-ray absorptive compounds composed of the above described aminium salt have the maximum absorption at a wavelength longer than 900 nm, and the absorption coefficient of the absorption peak of as high as approximately several hundred thousands. Such IR-ray absorptive compounds are also useful for heat insulation films and sunglasses, in addition to their primary use in optical recording media.

Incorporation of the IR-ray absorptive compounds of the present invention in an optical recording medium imports high heat stability and light resistance to the medium. Although the IR-ray absorptive compound may be incorporated singly into a recording layer, it is preferably incorporated together with other optical recording-type IR-ray absorptive coloring matters for the purpose of raising the sensitivity and reflectivity of the recording layer. The infrared light absorbing coloring matter which may be used in combination with the IR-ray absorptive compound of the present invention, include those which are generally known as coloring matters for optical recording. In particular coloring matters of the cyanine, merocyanine, chroconium, squarium, azulenium, polymethine naphthoquinone, pyrylium and, phthalocyanine types, etc., are preferred.

The IR-ray absorptive compound of formula (I) is, used based on the solid matter, in the range of from 1 to 60% by weight (preferably 5 to 40% by weight, more preferably 10 to 30% by weight) of the recording layer.

In addition to these compounds, a binder may be incorporated in the recording layer comprising a thin film of an organic coloring matter. The binders include cellulose esters such as nitrocellulose, cellulose phosphate, cellulose sulfate, cellulose acetate, cellulose propionate, cellulose butyrate, cellulose myristate, cellulose palmitate, cellulose acetate propionate, cellulose acetate butyrate, etc.; cellulose ethers such as methylcellulose, ethylcellulose, propylcellulose, butylcellulose, etc.; vinyl resins such as polystyrene, polyvinyl chloride, polyvinyl acetate, polyvinylbutyral, polyvinylacetal, polyvinyl alcohol, polyvinylpyrrolidone, etc.; copolymer resins such as a styrene-butadiene copolymer, a styrene-acrylonitrile copolymer, a styrene-butadiene-acrylonitrile copolymer, a vinyl chloride-vinyl acetate copolymer, etc.; acrylic resins such as polymethyl methacrylate, polymethyl acrylate, polybutyl acrylate, polyacrylic acid, polymethacrylic acid, polyacrylamide, polyacrylonitrile, etc.; polyesters such as polyethylene terephthalate; polyarylate resins such as poly(4,4'-isopropylidenediphenylene-co-1,4-cyclochexylenedimethylene carbonate), poly(ethylenedioxy-3,3'-phenylene thiocarbonate), poly(4,4'-isopropylidenediphenylene carbonate-co-terephthalate), poly(4,4'-isopropylidenediphenylene carbonate), poly(4,4'-sec-butylidenediphenylene carbonate, poly(4,4-isopropylidenediphenylene carbonate-block-oxyethylene), etc.; polyamides, polyimides, epoxy resins, phenol resins; and polyolefins such as polyethylene, polypropylene, chlorinated polyethylene, etc.

In the recording layer, there may also be added a surfactant, an antistatic agent, a stabilizer, a dispersion-type fire retardant, a slipping agent, or a plasticizer, etc.

A subbing layer may be provided between a recording layer and a substrate. Additionally, a protective layer may be provided on a recording layer. The subbing layer is provided for the purpose of imparting solvent resistance, improving reflectivity, and improving repetitive reproducibility. The protective layer is provided for the purpose of protecting the recording layer from scratch, dust, and dirt, and of imparting environmental stability to the recording layer. The materials mainly used for this purpose are inorganic compounds, metals, or organic high molecular weight compounds. The inorganic compounds includes $SiO_2$, $MgF_2$, SiO, $TiO_2$, ZnO, TiN, SiN, etc. The metals include Zn, Cu, Ni, Al, Cr, Ge, Se, Cd, etc. The organic high molecular weight compounds include ionomer resins, polyamide resins, vinyl resins, natural high molecular weight compounds, epoxy resins, silane coupling agents, etc.

The materials for the substrates include plastics such as polyesters, polycarbonates, acrylic resins, polyolefin resins, phenol resins, epoxy resins, polyamides, polyimides, etc.; glass and metals.

The organic solvent for coating is selected depending on the desired state of dispersion or dissolution. Generally the solvents used include alcohols such as methanol, ethanol, isopropanol, diacetone alcohol, etc.; ketones such as acetone, methyl ethyl ketone, cyclohexanone, etc.; amides such as N,N-dimethylformamide, N,N-dimethylacetamide, etc.; sulfoxides such as dimethylsulfoxide, etc.; ethers such as tetrahydrofuran, dioxane, ethyleneglycol monomethyl ether, etc.; esters such as methyl acetate, ethyl acetate, butyl acetate, etc.; aliphatic halogenated hydrocarbons such as dichloroethane, chloroform, methylene chloride, dichloroethylene, carbon tetrachloride, trichloroethylene, etc.; aromatic hydrocarbons such as benzene, toluene, xylene, monochlorobenzene, dichlorobenzene, etc.; and aliphatic hydrocarbons such as n-hexane, cyclohexane, ligroin, etc..

Coating may be conducted by dip coating, spray coating, spinner coating, bead coating, wire-bar coating, blade coating, roller coating, curtain coating, etc.

The thickness of the recording layer formed by use of the above solvent is suitably from 50 Å to 100 μm, preferably from 200 Å to 1 μm.

As described above, the IR-ray absorptive compounds of the present invention represented by formula (I) have a large absorption in the infrared region, and have improved solvent solubility and excellent characteristics because of the decreased linearity of the molecule.

By incorporating the IR-ray absorptive compound into a thin film containing an organic coloring matter of an optical recording medium, the storage stability noticeably improves, as does the light resistance of the medium. Further, the high solubility in solvents prevents formation of a solid matter such as fine crystals in the recording layer during the formation of the recording layer of the optical recording medium when a wet coating process is utilized, whereby an optical recording medium having a desirably low noise level can be obtained.

EXAMPLES

The examples below are intended to illustrate specific embodiments of the present invention.

Synthesis Example 1

0.1 mole of m-phenylenediamine, 0.5 mole of p-nitrochlorobenzene, 0.24 mole of anhydrous potassium carbonate, and 2 parts by weight of powdery copper in 130 parts of dimethylformamide was refluxed with stirring for 4 days. After the reaction, the reaction mixture was filtered. The filtered matter was washed with dimethyformamide, water, and acetone, and was dried to obtain 26 parts of tetrakis(p-nitrophenyl)-1,3-phenylenediamine of reddish brown color.

24 parts of the above prepared compound prepared above together with 100 parts of dimethylformamide and 1.5 parts of palladium-carbon hydrogenation catalyst, were put into an autoclave, and the mixture was stirred with supply of hydrogen at a pressure of 5.0 $kg/cm^2$ at 90°–100° C. until hydrogen absorption ceased.

The reaction mixture was filtered and the separated solid matter was washed with dimethylformamide. The filtrate was poured into 360 parts of ice water. After stirring for some time, the precipitate was collected by filtration. It was crystallized from an ethanol-dimethyformamide mixed solvent to obtain 10 parts of tetrakis(p-aminophenyl)-1,3-phenylenediamine. The purity was 98.5% according to high speed liquid chromatography.

Synthesis of Compound No. I-2

4 parts of the above described amino compound together with 24 parts of dimethylformamide, 0.7 part of anhydrous sodium hydrogencarbonate, and 4.0 parts of n-butyl bromide was heated with stirring at 100° C.–130° C. After 36 hours of reaction, the reaction mixture was poured into 150 parts of ice water, and the mixture was extracted with ethyl acetate. The extract was dried, and purified by employing a silica gel column. The yield of the product was 3.1 parts. The NH stretching vibration of the amino group was confirmed to have disappeared according to IR absorption analysis.

One part of this compound was dispersed in 20 parts of acetone, and thereto the equivalent moles of silver perchlorate was added with stirring. After reaction for 1 hour at a room temperature, the deposited silver was filtered off. The filtrate was diluted with isopropyl ether, and left standing. The deposited crystalline matter was collected by filtration. The yield was 0.6 part.

The compound No. I-2 thus synthesized had a large absorption band at an infrared region with the maximum absorption wavelength of 1004 nm, and absorption coefficient of 42,000.

The description above is made regarding the compounds having perchlorate as the anion. If the other anion is desired, the intended compound can be easily obtained by employing a silver salt corresponding thereto. For example, silver salts such as $AgSbF_6$, $AgBF_4$, $Ag_2SO_4$, $AgNO_3$, $AgSO_3C_6H_4CH_3$, $AgSO_3CF_3$, etc. may be used. Otherwise, the compounds can be prepared by electrolytic oxidation.

Synthesis of Compound No. I-7

2 parts of the amino compound prepared in Synthesis example 1 together with 12 parts of dimethylformamide, 0.4 parts of anhydrous sodium hydrogencarbonate, and 2.8 parts of allyl bromide were heated with stirring at 100° C.–130° C. After 36 hours of reaction, the reaction mixture was poured into 100 part of ice water, and the mixture was extracted with ethyl acetate. The extract was dried, and purified by employing a silica gel column. The yield of the product was 2.5 parts. The NH stretching vibration of the amino group was confirmed to have disappeared according to IR absorption analysis.

One part of this compound was dispersed in 20 parts of acetone, and thereto the equivalent moles of silver perchlorate was added with stirring. After reaction for 1 hour at a room temperature, the deposited silver was filtered off. The filtrate was diluted with isopropyl ether, and left standing. The deposited crystalline matter was collected by filtration. The yield was 0.7 part.

The compound thus synthesized had the maximum absorption wave length of 1108 nm.

Synthesis of Compound No. I-38

3 parts of the amino compound obtained in Synthesis example 1 together with 18 parts of dimethylformamide, 0.6 part of anhydrous sodium hydrogencarbonate, and 9 parts of 2,5-dibromohexane were heated with stirring at 100° C.–130° C. After 36 hours of reaction, the reaction mixture was poured into 120 part of ice water, and the mixture was extracted with ethyl acetate. The extract was dried, and purified by employing a silica gel column. The yield of the product was 4 parts. The NH stretching vibration of the amino group was confirmed to have disappeared according to IR absorption analysis.

One part of this compound was dispersed in 15 parts of acetone, and thereto the equivalent moles of silver hexafluoroantimonate was added with stirring. After reaction for 1 hour at a room temperature, the deposited silver was filtered off. The filtrate was diluted with isopropyl ether, and left standing. The deposited crystalline matter was collected by filtration. The yield was 0.8 part. The compound thus synthesized had a large absorption band at an infrared region with the maximum absorption wavelength of 1122 nm, and absorption coefficient of 57,000.

The examples are described below in which the IR-ray absorptive compounds of the general formula (I) are utilized as optical recording mediums.

Example 1

On a substrate of 130 mm in diameter and 1.2 mm in thickness made of polymethyl methacrylate (hereinafter referred to as PMMA), a layer of a ultraviolet-curing epoxy-acrylate type resin was provided in a thickness of 50 μm. A stamper having a pattern corresponding to a spiral pregroove having a width of 0.6 μm, a pitch of 1.6 μm, and a depth of 700 Å was brought closely into contact with the layer, and thereon ultraviolet radiation was applied to cure the layer to form a pregroove.

On the face having the formed pregroove, a dichloroethane in which a polymethine dye (IR-820, made by Nippon Kayaku K.K.) and the above described IR-ray absorptive compound No. I-2 were dissolved in a weight ratio of 90:10 was applied by spin coating to provide a recording layer of 800 Å thick. The medium thus prepared was sticked together with the other PMMA substrate with interposition of 0.3 mm spacers at the inner periphery side and the outer periphery side by use of an ultraviolet-curing resin adhesive to give an optical recording medium of air-sandwich structure.

With the optical recording mediums being rotating at a rate of 1800 rpm, recording was conducted by the use of a semiconductor laser of wavelength of 830 nm with recording power of 6 mW and recording frequency of 3 MHz from the substrate side. Subsequently reproduction was conducted with a readout power of 0.8 mW, and the C/N ratio was measured by spectrum analysis. Thereafter 100 thousand times of readout (namely, repetition of reproduction) was conducted. The C/N ratio after the repeated reproduction was measured.

Separately, the optical recording medium prepared as mentioned above was exposed to xenon lamp light of 1 KW/m² for 100 hours to test the light stability. After the exposure, the reflectivity and the C/N ratio were measured. The results are shown in Table 1.

TABLE 1

| Initial | | After repeated reproduction | After light stability test | |
|---|---|---|---|---|
| Reflectivity (%) | C/N (dB) | C/N (dB) | Reflectivity (%) | C/N (dB) |
| 24.7 | 56 | 54 | 22.8 | 53 |

Example 2

Onto the same substrate as the one in Example 1, a recording layer was provided by the use of a solution containing 1-guiazulenyl-5-(6'-t-butylazulenyl)-2,4-pentadienium perchlorate and the above mentioned IR-ray absorptive compound No. I-7 in a weight ratio of 90:10 in the same manner as in Example 1, to prepare a recording medium.

The optical recording mediums prepared thus were subjected to the same tests as in Example 1. The results are shown in Table 2.

TABLE 2

| | Initial | | After repeated reproduction | After light stability test | |
|---|---|---|---|---|---|
| | Reflectivity (%) | C/N (dB) | C/N (dB) | Reflectivity (%) | C/N (dB) |
| | 27.5 | 57 | 55 | 23.5 | 53 |

Examples 3-7

Optical recording mediums which contains the organic coloring matter and the IR-ray absorptive compound as shown in Table 3 were prepared and tested in the same manner as in Example 1. The test results are shown in Table 4.

TABLE 3

| Example No. | Organic coloring matter (A) | IR-ray absorptive compound (B) | Ratio A/B by weight |
|---|---|---|---|
| 3 | 1,5-Diguaiazulenyl-2,4-pentadienium perchlorate | I - 1 | 90:10 |
| 4 | (p-dibutylaminophenyl)-(p-methoxyphenyl)methylene-1-cyclopenten-2-yl-3-(p-dibutylaminophenyl)-(p-ethoxyphenyl)carbonium perchlorate | I - 8 | 80:20 |
| 5 | 1,5-bis(dipropylaminophenyl)-1,5-diphenyl-2,4-pentadienium perchlorate | I - 16 | 90:10 |
| 6 | 1,1'-dimethoxyethyl-3,3,3'3'-tetraethyl-2,2'-indotricarbocyanine perchlorate | I - 9 | 70:30 |
| 7 | NK-1414 (made by Nippon Kanko Sikiso K.K.) | I - 3 | 75:25 |
| 8 | 1,1,5,5-tetrakis-(p-dimethylaminophenyl)-2,4-pentadienium perchlorate | I - 31 | 85:15 |

Comparative Examples 1-3

Optical recording mediums were prepared and evaluated in the same manner as in Examples 1, 2, and 5 except that the IR-ray absorptive compounds in Examples 1, 2, and 5 were not used. The results are shown in Table 4.

TABLE 4

| | Initial | | After repeated reproduction | After light stability test | |
|---|---|---|---|---|---|
| Example No. | Reflectivity (%) | C/N (dB) | C/N (dB) | Reflectivity (%) | C/N (dB) |
| 3 | 26.9 | 55 | 53 | 22.5 | 51 |
| 4 | 25.3 | 54 | 52 | 20.1 | 50 |
| 5 | 25.5 | 57 | 56 | 20.6 | 54 |
| 6 | 35.0 | 53 | 52 | 29.7 | 51 |
| 7 | 32.1 | 51 | 49 | 19.9 | 48 |
| 8 | 26.3 | 54 | 52 | 23.8 | 52 |
| Comparative example No. | | | | | |
| 1 | 19.7 | 53 | 47 | 13.4 | 33 |
| 2 | 28.0 | 56 | 50 | 15.0 | 34 |
| 3 | 25.5 | 55 | 48 | 13.8 | 31 |

Examples 9-13

Pregrooves are provided on a substrate polycarbonate having a wallet size of 85 mm in length, 54 mm in width, and 0.4 mm in thickness (hereinafter referred to as PC) according to a hot press method. Thereon a solution of an organic coloring matter and an IR-ray absorptive compound shown in Table 5 below in diacetone alcohol was applied according to bar coating, and dried to obtain a recording layer of 850 Å thick.

Onto the recording layer, a hot melt adhesive sheet of ethylene-vinyl acetate type was laminated. Further thereon a PC protective plate of an wallet size and 0.3 mm thick was superposed, and the superposed matter was passed through a pair of rollers kept at the surface temperature of 110° C., to prepare an optical card of closely contacted encapsulation type without an air gap.

The optical recording medium of each of the above Examples was mounted on a stage driven in X and Y directions. Onto the organic thin recording layer, information was written in from the 0.4-mm thick PC substrate side by employing a semiconductor laser of oscillation wavelength of 830 nm with recording power of 4.0 mW and recording pulse of 80 μsec in the direction of Y axis. The information was reproduced with a read-out power of 0.4 mW, and the contrast ratio (A − B)/A was measured (where A is the signal strength at non-recorded portion, and B is the signal strength at the recorded portion).

Separately the same optical recording mediums prepared under the above mentioned conditions were tested for light stability in the same manner as in Example 1. The reflectivity and the contrast ratio after the light exposure were measured. The results are shown in Table 6.

TABLE 5

| Example No. | Organic coloring matter (A) | IR-ray absorptive compound (B) | Ratio A/B by weight |
|---|---|---|---|
| 9 | IR-820 (Made by Nippon Kayaku K.K.) | I - 28 | 85:15 |
| 10 | (p-Diethylaminophenyl)-(p-methoxyphenyl)methylene-1-cyclopenten 2-yl-3-(p-diethylaminophenyl)-(p-methoxyphenyl)carbonium perchlorate | I - 13 | 90:10 |
| 11 | 1,5-bis(dipropylaminophenyl)-1,5-diphenyl-2,4-pentadienium perchlorate | I - 4 | 75:25 |
| 12 | 1-Guaiazulenyl-5,5-bis(dimethyaminophenyl)-2,4-pentadienium perchlorate | I - 14 | 80:20 |
| 13 | 1,3-bis(diethylaminophenyl)-1,3-diphenylvinylcarbonium perchlorate | I - 38 | 70:30 |

Comparative Examples 5 and 6

Optical recording mediums were prepared and evaluated in the same manner as in Examples 10 and 13 except that the IR-ray absorptive compounds in Examples 10 and 13 were not used. The results are shown in Table 6.

TABLE 6

| Example No. | Initial | | After light stability test | |
|---|---|---|---|---|
| | Reflectivity(%) | Contrast ratio | Reflectivity(%) | Contrast ratio |
| 9 | 14.8 | 0.54 | 12.8 | 0.50 |
| 10 | 15.0 | 0.53 | 13.5 | 0.49 |
| 11 | 15.2 | 0.52 | 13.4 | 0.49 |
| 12 | 15.1 | 0.53 | 13.2 | 0.49 |
| 13 | 14.9 | 0.52 | 13.0 | 0.49 |
| Comparative Example No. | | | | |
| 5 | 15.7 | 0.77 | 8.9 | 0.48 |
| 6 | 15.4 | 0.68 | 10.2 | 0.41 |

We claim:

1. An optical recording medium comprising a recording layer containing an IR-ray absorptive compound represented by formula (I):

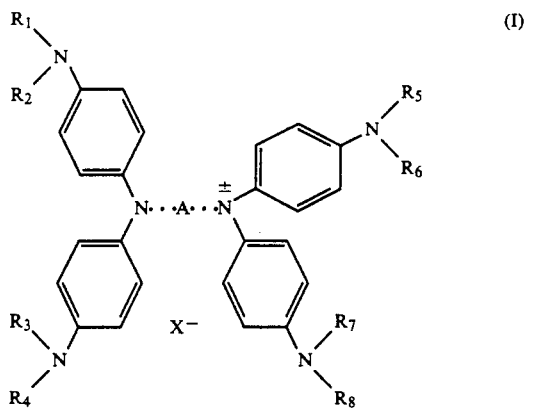

wherein A is

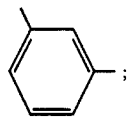

$R_1$ to $R_8$ are hydrogen, halogen, or a univalent organic radical, or at least one of the combinations of the atomic groups of $R_1$ and $R_2$, $R_3$ and $R_4$, $R_5$ and $R_6$, and $R_7$ and $R_8$ forms together with the nitrogen a substituted or unsubstituted five-, six- or seven-membered heterocycle; $R_1$ to $R_8$ being the same or different, and the combinations of $R_1$ and $R_2$, $R_3$ and $R_4$, $R_5$ and $R_6$, and $R_7$ and $R_8$ being the same or different; and $X^-$ is an anion.

2. An optical recording medium according to claim 1, wherein the compound of the formula (I) is contained in an amount of from 1 to 60% by weight based on the total solid in said recording layer.

3. An optical recording medium according to claim 2, wherein the compound of the formula (I) is contained in an amount of from 5 to 40% by weight based on the total solid in said recording layer.

4. An optical recording medium according to claim 3, wherein the compound of the formula (I) is contained in an amount of from 10 to 30% by weight based on the total solid in said recording layer.

5. An optical recording medium according to claim 1, further comprising a protective layer on said recording layer.

6. An optical recording medium according to claim 1, wherein the recording layer is formed by wet coating.

* * * * *

UNITED STATES PATENT AND TRADEMARK OFFICE
CERTIFICATE OF CORRECTION

PATENT NO. : 5,024,917
DATED : June 18, 1991
INVENTOR(S) : CHIEKO MIHARA, ET AL.

It is certified that error appears in the above-identified patent and that said Letters Patent is hereby corrected as shown below:

IN [54] TITLE and COL. 1, line 1-4:

"ALUMINIUM-TYPE" should read --AMINIUM-TYPE--.

IN [57] ABSTRACT

Line 7, "In corporation" should read --Incorporation--.
Line 11, "Further" should read --Further,--.

COLUMN 1

Line 3, "ALUMINIUM-TYPE" should read --AMINIUM-TYPE--.
Line 58, "improved" should read --with improved--.

COLUMN 2

Line 44, "molecule such that the," should read
--molecule, such that the--.

COLUMN 4

Line 38, "$ClO_4$-," should read --$ClO_4$-,--.

COLUMN 13

Line 62, "imports" should read --imparts--.

COLUMN 14

Line 58, "chroconium," should read --croconium,--.
Line 61, "pyrylium and," should read --pyrylium, and--.
Line 62, "is," should read --is--.
Line 63, "used" should read --used,--.

UNITED STATES PATENT AND TRADEMARK OFFICE
CERTIFICATE OF CORRECTION

PATENT NO. : 5,024,917
DATED : June 18, 1991
INVENTOR(S) : CHIEKO MIHARA, ET AL.

It is certified that error appears in the above-identified patent and that said Letters Patent is hereby corrected as shown below:

COLUMN 17

Line 27, "100 part" should read --100 parts--.
    Line 58, "120 part" should read --120 parts--.

COLUMN 19

Line 8, "Examples 3-7" should read --Examples 3-8--.

Signed and Sealed this

First Day of December, 1992

Attest:

DOUGLAS B. COMER

Attesting Officer      Acting Commissioner of Patents and Trademarks